(12) United States Patent
Yamakawa

(10) Patent No.: US 6,423,971 B1
(45) Date of Patent: Jul. 23, 2002

(54) EMISSION COMPUTED TOMOGRAPHY THROUGH THE DETECTION OF PAIRED GAMMA RAYS

(75) Inventor: Tsutomu Yamakawa, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/515,885

(22) Filed: Feb. 29, 2000

(30) Foreign Application Priority Data

Mar. 1, 1999 (JP) .......................................... 11-053041

(51) Int. Cl.[7] .............................................. G02B 23/00
(52) U.S. Cl. ................................................. 250/363.03
(58) Field of Search ..................................... 250/363.03

(56) References Cited

U.S. PATENT DOCUMENTS 3,787,685 A * 1/1974 Grenier ....................... 250/394
3,865,976 A * 2/1975 Grenier ....................... 178/18.07
5,760,401 A * 6/1998 Nelleman et al. ........ 250/363.03
5,970,499 A * 10/1999 Smith et al. ................. 707/104

* cited by examiner

*Primary Examiner*—Georgia Epps
*Assistant Examiner*—Alicia M Harrington
(74) *Attorney, Agent, or Firm*—Oblon, Spivak, McClelland, Maier & Neustadt, P.C.

(57) ABSTRACT

The present invention calculates incidence directions of gamma rays by an incidence direction calculating circuit on the basis of the incidence directions of gamma rays to detectors. And a planar image generating circuit generates planar image data on the basis of count data relating to an event coincident or near-coincident with an incidence direction designated by an operator on an input device.

20 Claims, 6 Drawing Sheets

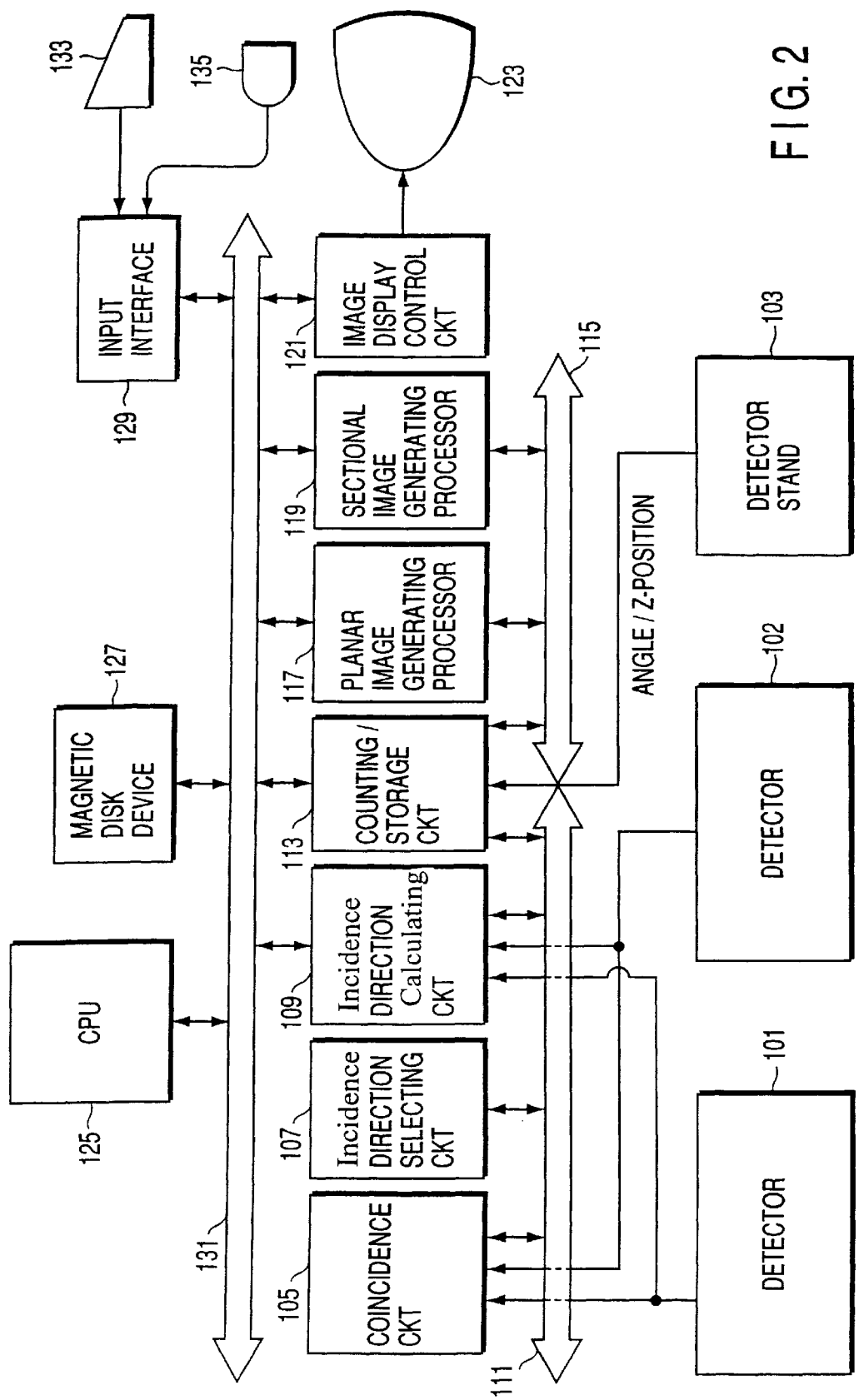
F I G. 2

EMISSION COMPUTED TOMOGRAPHY THROUGH THE DETECTION OF PAIRED GAMMA RAYS

CROSS-REFERENCE TO RELATED APPLICATION

This application is based upon and claims the benefit of priority from the prior Japanese Patent Application No. 11-053041, filed Mar. 1, 1999, the entire contents of which are incorporated herein by reference.

BACKGROUND OF THE INVENTION

The present invention relates to a nuclear medicine diagnostic apparatus for repeatedly measuring, while varying the angles of detectors relative to a subject, gamma rays which are emitted from RI (Radio-Isotope) injected into a subject and reconstructing an RI distribution (hereinafter referred to as a sectional image) based on data collected thereby. This type of nuclear medicine diagnostic apparatus is called as an ECT (Emission Computed Tomography) to be distinguished from an X ray computed tomography apparatus.

In the ECT, there are a method using a single photon RI such as $^{99m}TC$ and $^{111}In$ and a method using a positron RI such as FDG, $^{11}C$ and $^{13}N$. The former is called a SPECT (Single Photon Emission Computed Tomography) and the latter as a PET (Positron Emission Computed Tomography). The positron emitted by a beta disintegration from the positron RI used in the PET is annihilated through a combination with an electron. At this time, two annihilated photons (gamma rays) of 511 keV are radiated in mutually opposite directions. The PET apparatus selects the paired gamma rays based on the coincidence and has the function of locating the position of the presence of the positron RI and, accurately, the annihilation position of the positron.

FIG. 1 is a view diagrammatically showing a structure of a conventional PET apparatus. In order to detect paired annihilation gamma rays emitted in opposite directions, two detectors 1, 2 are arranged opposite to each other with a subject P interposed. Parallel multi-hole collimators are mounted on these two detectors 1, 2 so as to guide only gamma rays incident at a vertical or near-vertical angle to the two detectors. Not only paired annihilation gamma rays derived from the same annihilation phenomenon but also other gamma rays are randomly incident on the two detectors. Through the utilization of the coincidence between the output of one detector 1 and that of the other detector 2, a coincidence circuit selects the paired annihilation gamma rays and counts them at each incidence position. The count operation is interruptedly repeated while varying the angles of the detectors 1, 2 relative to the subject P on a little-by-little basis. Based on the data acquired through the repeated count operation, the RI density distribution (hereinafter referred to as a sectional image) of a sectional plane is generated by a reconstruction circuit 4. This sectional image is displayed on a display unit 5.

As this type of PET, some types have the function of generating a sectional image for positioning. The sectional image for positioning is shorter in counting time than the sectional image for diagnosis and coarser in matrix. In comparison with the sectional image for diagnosis, the sectional image for positioning shortens, to an about 1/n (n: natural number), a time from the data collection to an image display.

In order to achieve positioning, it is necessary to take a plurality of sectional images different in data collection positions. And it takes a long time to achieve such positioning.

BRIEF SUMMARY OF THE INVENTION

An object of the present invention is to enable a planar image to be utilized for a multi-purpose application, such as positioning, in a nuclear medicine diagnostic apparatus for reconstructing an RI distribution of a sectional plane of a subject, coincidence PET apparatus etc.

The present invention calculates the incidence directions of gamma rays by an incidence direction calculating circuit on the basis of an incidence positions of the gamma rays on the detectors. A planar image generating circuit generates planar image data on the basis of count data relating to an event coincident or near-coincident with the incident direction designated by an operator on an input device. A display unit displays a planar image on the basis of the planar image data generated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a block diagram of a PET apparatus according to an embodiment of the present invention;

DETAILED DESCRIPTION OF THE INVENTION

An embodiment of the present invention will be explained below. One type of nuclear medicine diagnostic apparatus, called a gamma camera, allows gamma rays that are emitted from an RI injected into a subject to be detected for a predetermined time period with the use of detectors stationary relative to the subject, and generates a projection distribution (hereinafter referred to as a planer image) on an RI detection surface on the basis of data collected thereby. Another type, called ECT (Emission Computer Tomography), allows gamma rays that are emitted from an RI injected into a subject to be repeatedly measured, while varying the angles of detectors relative to the subject, and reconstructing an RI distribution (hereinafter referred to as a sectional image) in a sectional plane on the basis of data collected thereby.

For ECT, there is an imaging method called SPECT (Single Photon Emission Computed Tomography) that uses a single photon RI, such as $^{99m}$TC and $^{111}$In, and an imaging method called PET (Positron Emission Computed Tomography) that uses a positron RI, such as FDG, $^{11}$C and $^{13}$N. The present invention relates to PET.

Further, devices configured for PET are of two types: a two-detector-facing type and a PET-only ring array type, in which a plurality of small-type detectors are arranged in a hexagonal or circular array. The present invention can be applied to any of these types. Hereinbelow, the two-detector-facing type will be explained by way of example.

FIG. 2 is a schematic diagram showing a PET apparatus according to a preferred embodiment of the present invention.

Figure 1:
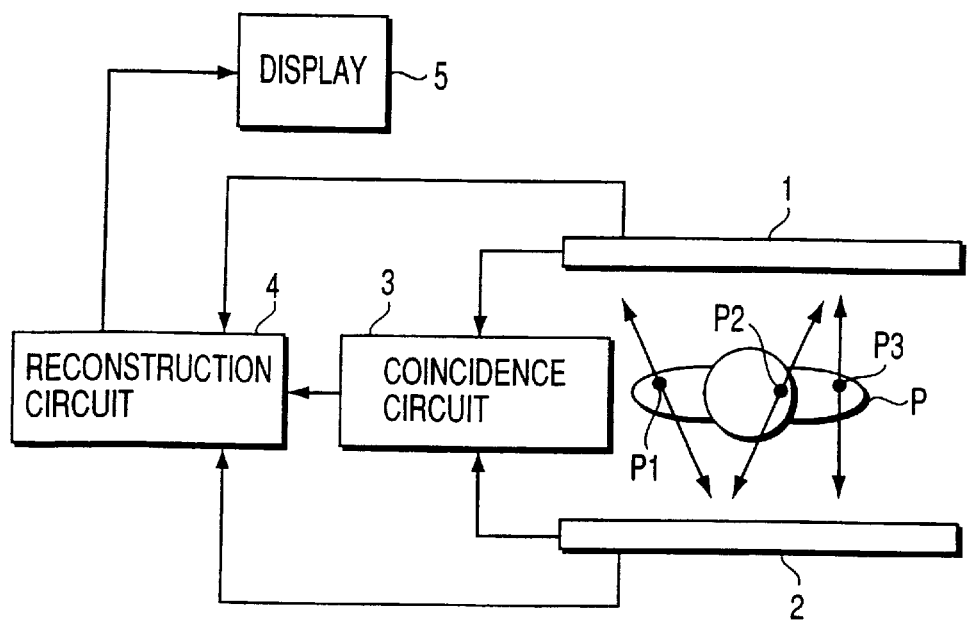
FIG. 1 is a schematic diagram showing a conventional PET apparatus.
Figure 3:
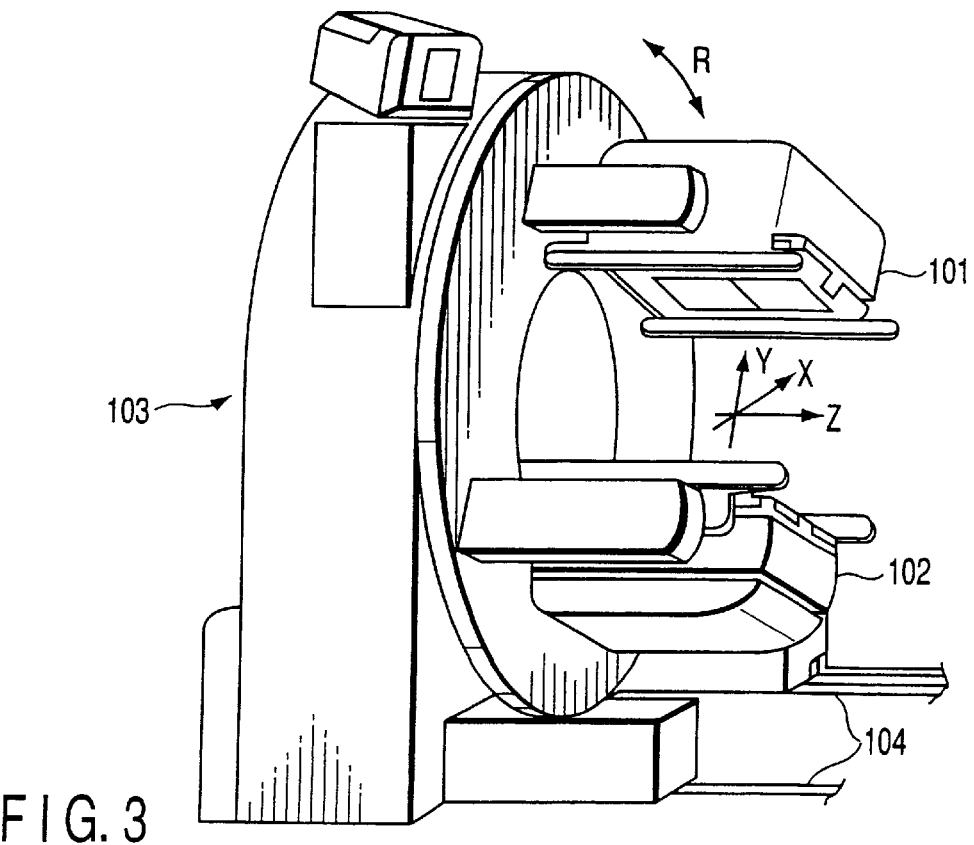
FIG. 3 is an outer appearance view showing a detector stand of FIG. 2.

FIG. 3 is an outer appearance view showing the detector stand in FIG. 2.

The detector stand 103 holds two detectors 101, 102 in a mutually facing position and is so configured as to be rotatable about a Z axis (arrow R) substantially coincident with a body axis of a subject while retaining its positional relation. Further, the detector stand 103 is arranged on rails 104 on a floor surface to be slidable along the Z axis.

The detectors 101, 102, respectively, have a plurality of semiconductor cells arranged in a matrix array so as to achieve a counting yield (true coincidence) of 100K cps. The respective semiconductor cell is made of cadmium telluride (CdTe) or cadmium zinc telluride (CdZnTe). The respective semiconductor cell may be comprised of a combination of a scintillator and photoelectric conversion element. The scintillator may be made of sodium iodide (NaI), LSO (Lutetium oxyorhosilicate), BGO (bismuth germanium oxide) or cesium iodide (CsI). The photoelectric conversion element is formed of, for example, a photodiode.

To the detection bus 111, a coincidence circuit 105, incidence direction calculating circuit 109, incidence direction selecting circuit 107 and counting/storage circuit 113 are connected. The detector stand 103 is connected to the counting/storage circuit 113 so that the counting/storage circuit 113 receives information relating to the angles of the detectors 101, 102 with respect to the subject and Z position (position of the detector stand 103 in the body axis direction). The counting/storage circuit 113 is connected also to an image bus 115. To the image bus 115, a planar image generating processor 117, sectional image generating processor 119 and image display control circuit 121 are connected. To the image display control circuit 121 a display unit 123 is connected. The coincidence circuit 105, incidence direction calculating circuit 109, incidence direction selecting circuit 107, counting/storage circuit 113, planar image generating processor 117, sectional image generating processor 119 and image display control circuit 121 are connected via a CPU bus 131 to a CPU 125 for controlling a system as a whole. To the CPU bus 131 a magnetic disk device 127 is connected to mainly store planar image data and sectional image data. Input devices including a keyboard 133 and mouse 135 are connected through an input interface 129 to the CPU 131.

The above-mentioned coincidence circuit 105 is connected directly to the detectors 101 and 102 and configured to select, out of all events involving detection of gamma rays by the detectors 101 and 102, an event (hereinafter referred to as a target event) of paired gamma rays derived from a positron RI injected into the subject and simultaneously detected by the detectors 101, 102. Stated in more detail, when, in a predetermined time window range from a timing in which gamma rays are detected by one detector 101 (or 102), gamma rays are detected by the other detector 102 (or 101), one pulse is generated, indicating that the event is the target event.

The incidence direction calculating circuit 109 is connected directly to the detectors 101, 102 and calculates, while taking the target event as a target, incidence directions of gamma rays to a detection surface of the detector 101 (or 102) on the basis of the incidence position of a detection surface of the detector 101 and incidence position of a detection surface of the detector 102. It is to be noted that the incidence positions of the detection surfaces of the detectors 101, 102 correspond directly to the positions of the semiconductor cells for outputting signals responsive to the incidences of gamma rays.

The incidence direction selecting circuit 107 selects, out of those target events, an event (hereinafter referred to as a specific event) at which the incidence direction calculated by the incidence direction calculating circuit 109 is coincident or near-coincident with the incident direction designated by the operator through the input devices 133, 135. The counting/storage circuit 118 counts the number of specific events at the respective positions and stores the corresponding data.

The planar image generating processor 117 generates, based on the counting data relating to a single angle stored in the counting/storage circuit 118, planar image data representing an RI density distribution projected on the detection surface of the detector 101 (or 102). The sectional image generating processor 119 generates (reconstructs) a sectional image data representing the RI density distribution within the sectional surface. The image display control circuit 121 generates, based on the generated planar image data and sectional image data, display image data corresponding to the display surface set by the operator via the input devices 133, 135.

Now, an explanation will be made about the function of the PET apparatus of the present embodiment.

The present apparatus can selectively generate two kinds of planar image data, that is, planar image data for positioning which is relatively coarse in a spatial resolution for setting a sectional position of a PET and planar image data for diagnosis which is relatively fine in a spatial resolution in comparison with the planar image data for positioning.

First, an explanation will be made about the function relating to the planar image data for positioning. The operator sets the angle of the detector 101 (or 102) relative to the subject and Z positions of the detectors 101, 102, respectively, to a desired angle and desired Z position via the input devices 133, 135. Further, the operator designates, through the input devices 133, 135, a desired incidence direction relating to the planar image data for positioning. Finally, planar image data relating to gamma rays incident from the designated incidence direction is created.

Figure 9A:
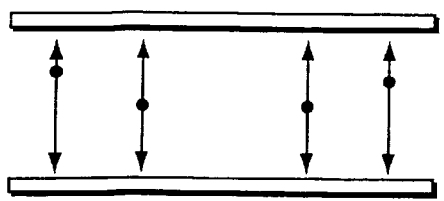
FIG. 9A is a view showing, in the present embodiment, incidence directions intersecting substantially vertical to detectors.
Figure 9C:
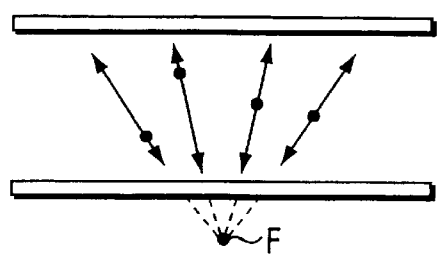
FIG. 9C is a view showing incident directions converging at one point.
Figure 9B:
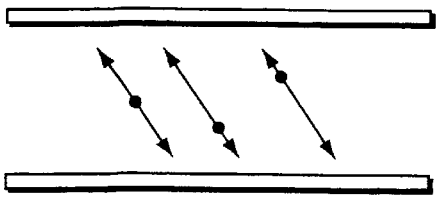
FIG. 9B is a view showing, in the present embodiment, incidence directions obliquely incident on the detectors.
Figure 9D:
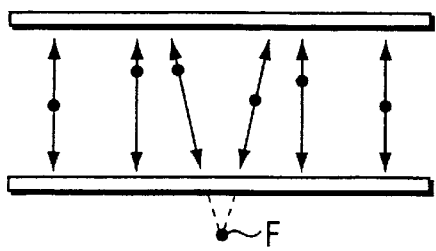
FIG. 9D is a view showing, in the present embodiment, a combination of incidence directions converging at one point and incidence directions substantially vertical or oblique to the detectors.

As the designated incidence directions, there are typically a direction intersecting substantially vertical relative to the detection surface and a direction intersecting obliquely relative to the detection surface as shown in FIGS. 9A and 9B. In the present embodiment, as shown in FIG. 9C, it is possible to designate the incidence directions as converging at one point. Further, as shown in FIG. 9D, it is possible to designate, in a combined way, the incidence directions as being vertical to one portion of the detection surface and converging at one point F at another portion as shown in FIG. 9D. It is possible to set the incidence direction freely. Further, it is possible to designate different incidence directions so that, finally, a plurality of planar images are created in different incidence directions.

Subsequent to the above-mentioned setting, a positron RI is actually injected into the subject and a detection operation by the detectors 101, 102 is started. Not only paired annihilation gamma rays derived from the positron RI but also extraneous gamma rays, etc., are incident on the detectors 101, 102. That is, the events of gamma rays detected by the detectors 101, 102 include a target event derived from the positron RI and a non-target-event not derived from the positron RI. Out of these, only the target event (true coincidence) is selected by the coincidence circuit 105 on the basis of the coincidence of the incidence timing (signal output timing) of the detector 101 and incidence timing of the detector 102.

Figure 4:
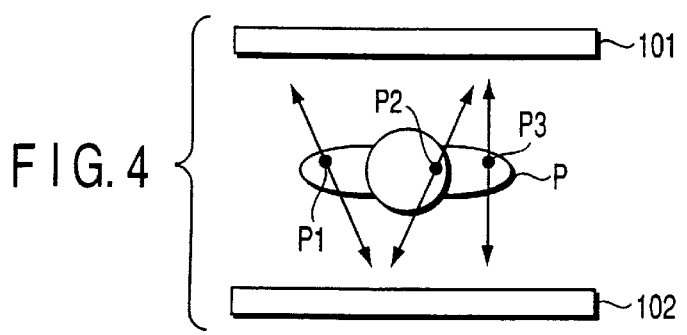
FIG. 4 is a view showing a flight line of paired gamma rays in the present embodiment.

Further, the incidence direction of the target event is various as shown in FIG. 4. Out of those target events, a specific event at which an incidence direction (for example, an incidence direction P1 in FIG. 4) calculated by the incidence direction calculating circuit 109 is coincident with the incidence direction designated by the operator, or the difference between both the directions is smaller than a predetermined value, is selected.

The specific event thus selected is counted by the counting/storage circuit 118 at each incidence position. The count data is stored in the counting/storage circuit 118.

The detection, selection and counting operations are continued for a predetermined period. This period is generally called a data storage period or data collection period. The data storage period for the planar image data for positioning is shorter than a data storage period for planar image data for diagnosis as will be set out below.

In order to suppress a low image density resulting from the short data storage time, the counting for the planar image data for diagnosis is done using one semiconductor cell or a few neighboring semiconductor cells as one unit (as a single incidence position), while, on the other hand, the counting for the planar image data for positioning is done using, as one unit, those neighboring semiconductor cells greater in number than in the case where the counting of the planar image data for diagnosis is done. As a result, the spatial resolution of the planar image data for positioning becomes coarser than the spatial resolution of the planer image data for diagnosis, but it is sufficient when performing the function of deciding a sectional position.

After the passage of the data storage period, the planar image data for positioning is created by the planar image generating processor 117 on the basis of the counting data stored in the counting/storage circuit 118.

Although, in the above-mentioned explanation, the target events are selected based on the coincidence and, out of these events, a specific event of a designated incidence direction is selected and such specific event is counted at each incidence position, it may be possible that, during the data storage period, all the target events selected from the target events on the basis of the coincidence without selecting the specific event of a designated incidence direction are stored, together with information on the incidence position and calculated incidence direction, in the counting/storage circuit 113. In this case, after the data storage time period, a planar image of any given incidence direction can be created with the use of the stored data. That is, the planar image data is created based on the count data relating to an event whose calculated incidence direction is coincident or near-coincident with the incidence direction designated based on the data relating to the incidence position and calculated incidence direction of the target event stored in the counting/storage circuit 113. This operation of a high degree of freedom is applied not only at a time of data collection for the planar image for positioning but also at a time of data collection for the planar image for diagnosis as will be set out below.

Figure 5:
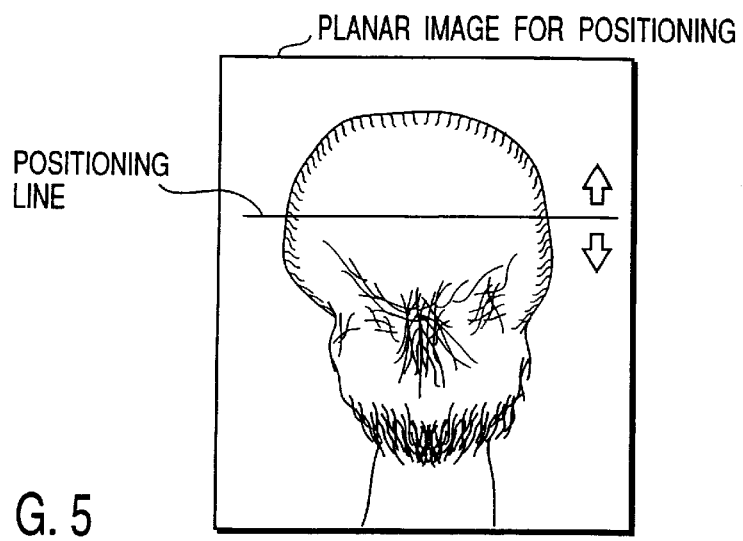
FIG. 5 is a view showing an example of a display of a planar image for positioning which is generated by a planar image generating processor of FIG. 2.

Based on the thus created planar image data for positioning, the display data is created by the image display control circuit 121. FIG. 5 is a display example of the planar image for positioning. As shown in FIG. 5, a positioning line is composed on the planar image for positioning. The positioning line can be moved up and down across an image screen, relative to the planar image for positioning, in accordance with an operation quantity of the input devices 133, 135. By operating the input devices 133, 135, the positioning line can be set on a desired position on the planar image for positioning. By doing so, it is possible to set a sectional position for collecting data necessary to reconstruct the sectional image data.

A plurality of sectional positions can be set so as to finally create a plurality of sectional images of different sectional positions.

In order to move the detector stand 103 to a set sectional position, the CPU 125 controls the detector stand 103 in accordance with the set sectional position. At that position, data collection for PET is carried out. The detector stand 103 sets the devices 101, 102 at an initial angle to a subject. The data collection operation is started at this angle.

Out of those events of gamma rays detected by the detectors 101, 102, a target event derived from the positron RI is selected by the coincidence circuit 105 on the basis of that coincidence. Out of these events, a specific event of gamma rays incident at a vertical or near-vertical incidence angle on the detection surfaces of the detectors 101, 102 for example is selected by the incidence direction selecting circuit 107.

The thus selected specific event is counted by the counting/storage circuit 118 at each incidence position and the count data is stored in the counting/storage circuit 118. The detection, selection and counting operations are continued for a predetermined data storage period. The data storage period for PET is longer than the data storage period for the planar image data for positioning as set out above and the spatial resolution is higher.

After the passage of the data storage period, the detector stand 103 rotates the detectors 101, 102 through a very small angle and data collection is similarly carried out. In this way, the rotation and data collection operation are done alternately. And based on the collection data corresponding to 360° the sectional image data is reconstructed by the sectional image generating processor 119.

Figure 6:
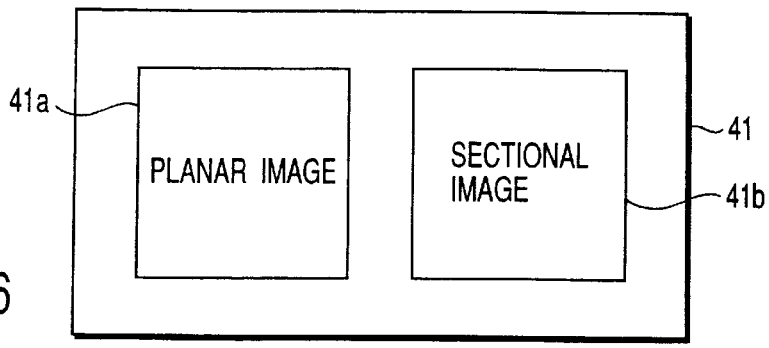
FIG. 6 is a view showing an example of a display in a present embodiment which displays, together with a PET sectional image, a planar image for positioning or referring.
Figure 7:
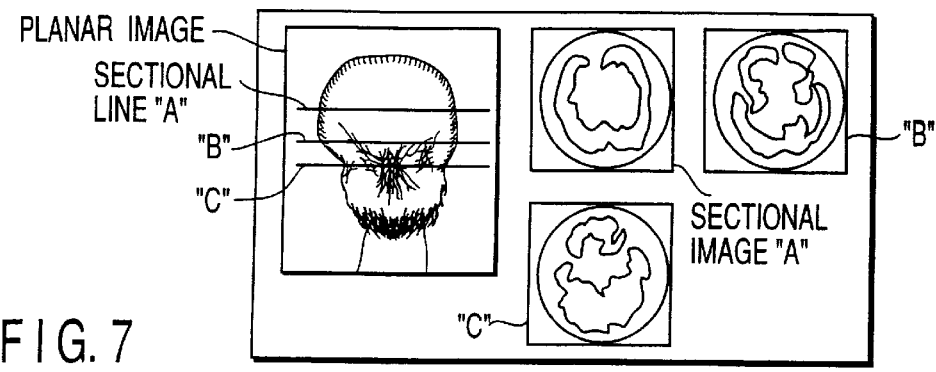
FIG. 7 is a view showing an example of a display in a present embodiment which displays, together with the planar display for positioning, a plurality of PET sectional images different in sectional positions.

Based on the sectional image data, the display data is generated at the image display control circuit 121. FIG. 6 shows an example of display. The sectional image may be singly displayed on the image screen or, as shown in FIG. 6, the sectional image, together with the planar image for positioning, may be displayed on the same image screen or another image screen. In this case, the positioning line is preferably composed on the planar image so as to enable the observer to identify the sectional position. Composing the positioning line on the planar image is particularly effective when, as shown in FIG. 7, a plurality of sectional images of different sectional positions are composed.

An explanation will be given below about the function relating to the generation of the planar image data for diagnosis. The operation relating to the data collection for the planar image data for diagnosis is basically the same as the operation relating to the data collection for the planar image data for positioning, but it is different in terms of being longer in data accumulation time and higher in spatial resolution and thus being smaller in counting units.

Here, as the incidence direction designated to generate the planar image data for diagnosis there are typically, as shown in FIGS. 9A and 9B, a direction intersecting substantially vertical to the detection surface and a direction intersecting obliquely with respect to the detection surface. According to the present embodiment, however, the incidence directions can be so designated as to converge at one point F as shown in FIG. 9C. As shown in FIG. 9D, it is possible to designate, in a combined way, the incidence directions as being vertical on a portion of the detection surface and converging at one point F relative to another portion.

Figure 8:
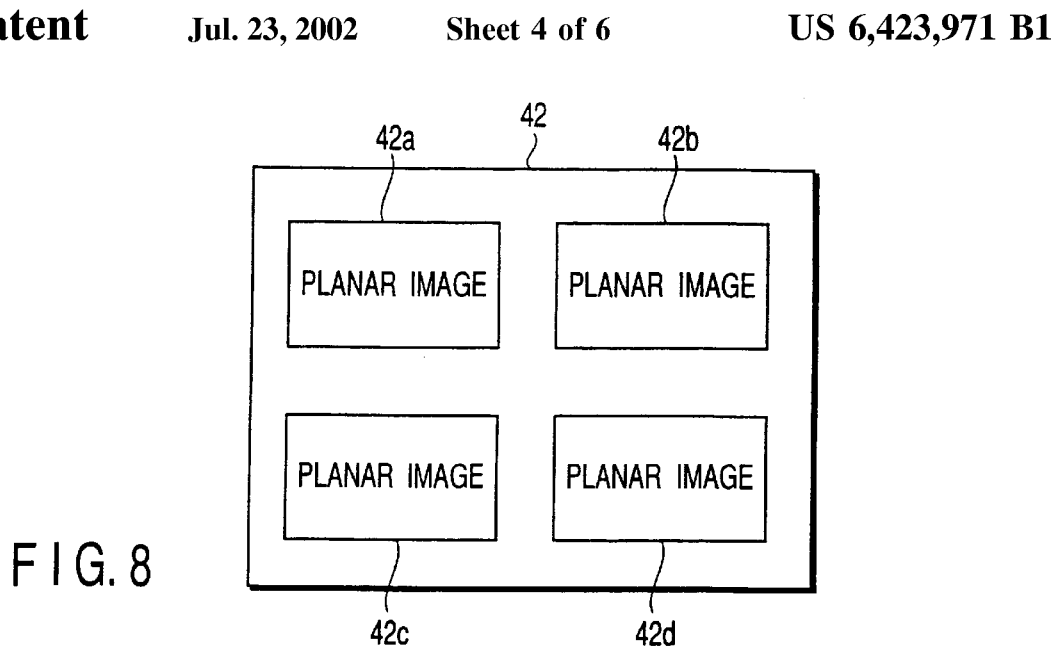
FIG. 8 shows an example of a display for displaying a plurality of planar images on the same image plane.
Figure 10:
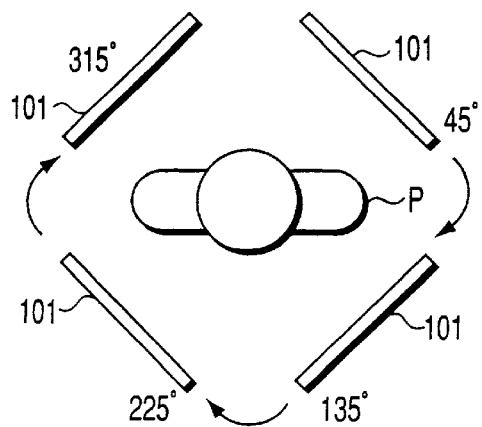
FIG. 10 shows four angles of detectors relative to a subject.

A plurality of different incidence directions can be designated so as to finally create a plurality of planar images different in incidence direction. These planar images different in incidence direction may be singly displayed on the image surface and they may be displayed simultaneously as shown in FIG. 8. As shown in FIG. 10, a plurality of planar images different in angle are created and these may be displayed singly or, as shown in FIG. 8, simultaneously.

Figure 11A:
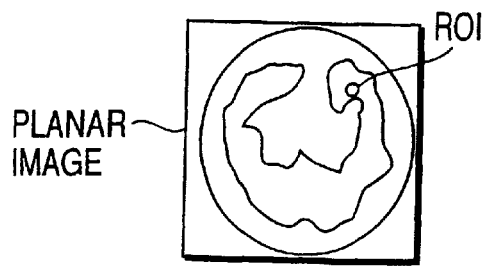
FIG. 11A is a view showing a region of interest (ROI) designated on a planar image.
Figure 11B:
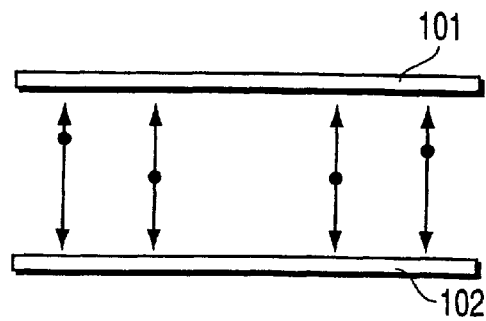
FIG. 11B is a view showing an incidence direction of the planar image of FIG. 11A.
Figure 12A:
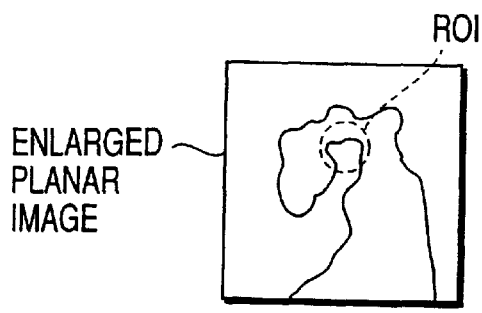
FIG. 12A is a view showing a planar view enlarged with the ROI of FIG. 11A as a center.
Figure 12B:
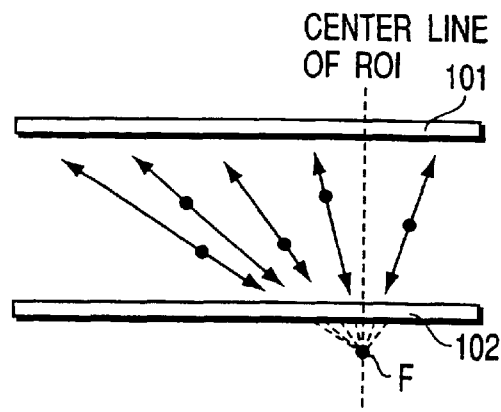
FIG. 12B is a view showing directions of an enlarged planar view of FIG. 12A.

As shown in FIGS. 11A and 11B, when a region of interest (ROI) is designated on a 100%-sized planar image corresponding to the vertical incidence direction, the planar image generating processor 113 has the function of setting the incidence directions as converging at one point F with the ROI as a center as shown in FIGS. 12A and 12B, creating an enlarged planar image corresponding to that image and switching the display of the 100%-sized planar image to that of the enlarged image. This function has a high possibility of enhancing the diagnostic efficiency and accuracy.

The data collection operation for the planar image for diagnosis is selectively performed independently of the data collection operation for the sectional image or simultaneously with the data collection operation for the diagnostic image. In the latter case, the data for the planar image for diagnosis can share a portion of the data collected by the data collection operation for the sectional image. In this case, the incidence direction of the planar image for diagnosis is restricted to the vertical or near-vertical angle incidence direction as in the case of the sectional image for PET. However, the incidence direction of the planar image for diagnosis can of course be set to the oblique incidence direction, converging incidence direction, etc., unlike in the case of the sectional image for PET. In this case, however, the direction selection and counting operations are performed in parallel with those for PET.

Figure 13:
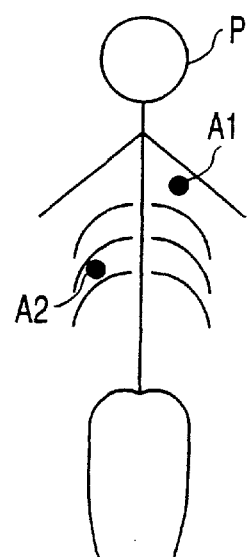
FIG. 13 is a view showing an example of whole body's planar image generated by a planar image generation processor of FIG. 2.

The above-mentioned planar image for positioning and planar image for diagnosis can be taken, by moving the detector stand 103, with a whole body as a target. The Z position information of the detectors 101, 102 are supplied from the detector stand 103 to the counting/storage circuit 118. The counting/storage circuit 118 counts the specific event at each incidence position and Z position. FIG. 13 is a view showing an example of display of a whole body's planar image collected by the present embodiment. In the case where a whole body's planar image representing a whole body's FDG distribution as shown in FIG. 13 is displayed on the display unit 123, it follows that if a doctor or operator judges tumors A1, A2 for example as being present while looking at this whole body's planar image, he or she will set these tumor (A1, A2)-present positions as sectional positions. By doing so, the operation relating to the setting of the sectional position can be completed for a shorter period of time in comparison with the conventional case where all PET sectional images have to be taken by performing the PET data collection of the whole body of the subject. Thus it is possible to reduce a checking time for the patient and to alleviate the burden on the patient, operator, etc. In this connection it is to be noted that the FDG represents the imaging of a glucose metabolism by an 18F-fluoro-2-deoxyglucose (one kind of positron product preparation) and is used for the differential diagnosis of malignant tumors.

Figure 14:
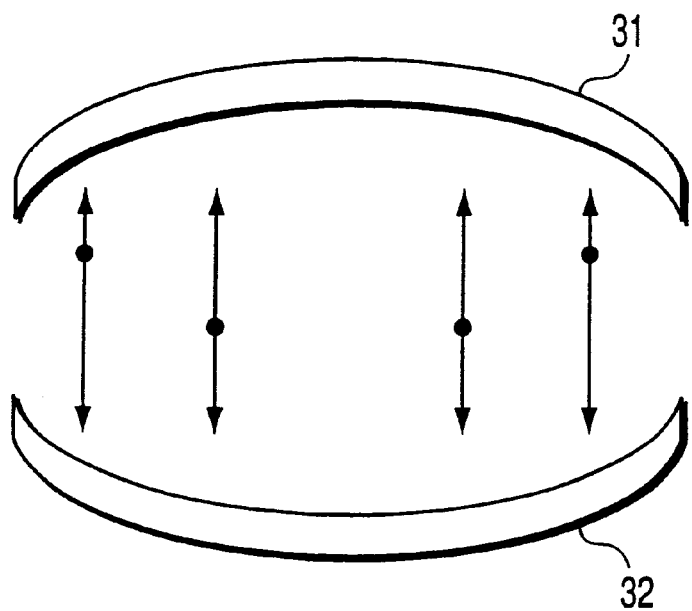
FIG. 14 is a view showing an example of another practical form of a second detector.

It is to be noted that, as shown in FIG. 14, the detectors 101, 102 may be so configured as to be outwardly convex (inwardly concave) relative to the subject. Even in this case, selecting a specific event corresponding to a desired incidence direction in accordance with the incidence directions calculated from two incidence positions is the same as the case where the detection surfaces of the detectors 101, 102 are planar.

Figure 15:
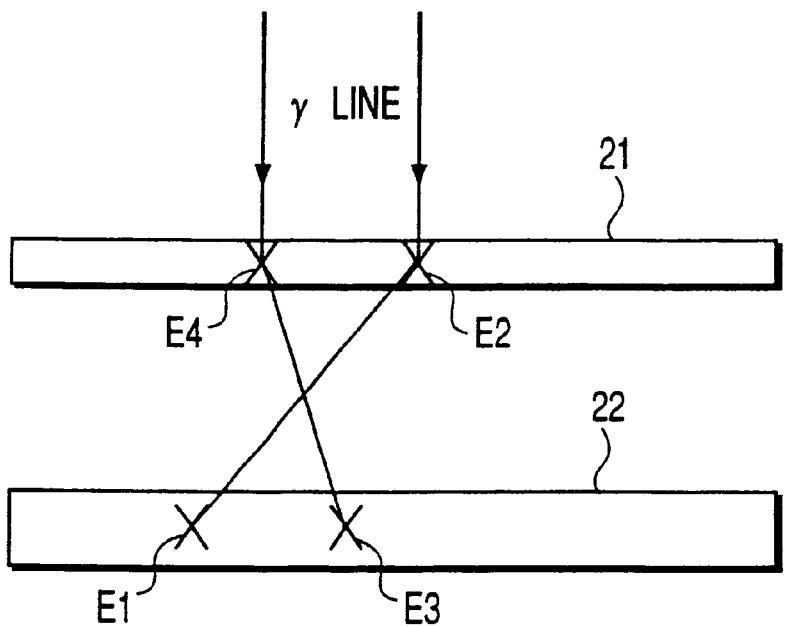
FIG. 15 is a view showing, in a variant, detectors compatible with a Compton camera.

Incidentally, the present invention can be applied to a Compton camera utilizing the Compton effect. As shown in FIG. 15, the detector of the Compton camera has a stacked scattering layer 21 and absorption layer 22. The Compton effect is such that gamma rays produce an elastic collision with electrons in the scattering layer as known in that field. The energy of the recoil electrons is given as Ee (E2, E4 in FIG. 15). And the energy of the scattering rays is detected by the absorption layer 22. This energy is given as Es. Let the incidence energy to be Er, the static energy (0.511 MeV) of the electron to be $mc^2$ and the scattering angle of the scattered rays to be θ. Then, the following relation is established:

$$Ee = Er - Es$$
$$= Er/(1 + (mc^2/(Er(1-\cos))))$$

Thus, the incidence angle of the gamma rays can be calculated from the position of the elastic collision in the scattering layer 21, absorption position within the absorption layer 22 and Ee, Er, Es. Gamma rays incident from an incidence angle 0°, that is, from a direction vertical to the detection surface are selected. A sectional image is reconstructed based on the count data of the selected specific event. Even for such a Compton camera it is possible to create planar image data corresponding to vertically incident gamma rays.

According to the present invention, it is possible to create a planar image with the PET apparatus and Compton camera. By doing so it is possible to obtain the following advantages:

(1) For the PET apparatus it is possible to set the sectional positions very simply and intuitively.

(2) For the PET apparatus for the whole body of the subject it is possible to readily decide only a requisite imaging area through the whole body's data collection.

(3) Since it is possible to display a requisite imaging area as an enlarged area, it is possible to enhance identification accuracy with which the subject is positioned for imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A nuclear medicine diagnostic apparatus for selecting, out of events involving detection of gamma rays by detectors, an event of paired gamma rays derived from a positron RI injected into a subject and simultaneously detected by the detectors and reconstructing sectional image data on the basis of count data relating to the selected event, comprising:

an input device configured to designate a desired incidence direction;

an incidence direction calculating circuit configured to calculate incidence directions of the gamma rays relating to the selected event on the basis of incidence positions of the gamma rays relating to the selected event;

a planar image generating circuit configured to generate planar image data on the basis of count data relating to an event whose calculated incidence direction is coincident or near-coincident with the designated incidence direction; and a displaying unit configured to display a planar image on the basis of the planar image data.

2. A nuclear medicine diagnostic apparatus according to claim 1, wherein the display unit displays, together with the planar image, a positioning line representing a position in which data necessary to generate the sectional image data is collected.

3. A nuclear medicine diagnostic apparatus according to claim 2, further comprising a unit configured to move the detector in accordance with a position which is set with the use of the positioning line.

4. A nuclear medicine diagnostic apparatus according to claim 1, wherein the displaying unit displays, together with the planar image, the sectional image on the same image screen or another image screen.

5. A nuclear medicine diagnostic apparatus according to claim 4, wherein the displaying unit displays, as a composed planar image, a sectional line representing a position in which the data necessary to generate the sectional image data is collected.

6. A nuclear medicine diagnostic apparatus according to claim 1, wherein the planar image generating circuit generates a plurality of planar images different in incidence directions and the displaying unit displays the planar images on a display screen.

7. A nuclear medicine diagnostic apparatus according to claim 1, wherein the planar image generating circuit generates a plurality of planar images different in angles of the detectors relative to the subject and the display unit displays the planar images on an image screen.

8. A nuclear medicine diagnostic apparatus according to claim 1, wherein the planar image generating circuit generates planar image data intersecting substantially in incident direction to the detectors, planar image data obliquely intersecting in incidence direction to the detectors or planar image data converging in incidence direction at one point.

9. A nuclear medicine diagnostic apparatus according to claim 1, wherein the planar image generating circuit generates planar image data as composite data including an image portion converging in incidence direction at one point and an image portion substantially vertical or oblique in incidence direction.

10. A nuclear medicine diagnostic apparatus according to claim 9, wherein the image portion converging in incidence direction at one point is a substantially central portion on a detection surface of the detector.

11. A nuclear medicine diagnostic apparatus according to claim 8, wherein the image portion converging in incidence direction at one point corresponds to a region of interest designated by the user.

12. A nuclear medicine diagnostic apparatus according to claim 1, wherein the planar image generating circuit generates a planar image converging in incidence direction at a position corresponding to the region of interest when the region of interest is designated in any given position on a planar image displayed substantially vertical or oblique in incidence direction and the displaying unit effects a switching display from a planar image substantially vertical or oblique in incidence direction to a planar image converging in incidence direction at a position corresponding to the region of interest.

13. A nuclear medicine diagnostic apparatus according to claim 1, wherein the planar image data is generated with the use of a portion of data collected for the sectional image data.

14. A nuclear medicine diagnostic apparatus according to claim 1, wherein the planar image generating circuit can generate planar image data coarse in a spatial resolution for setting a data collecting position for the sectional image data and planar image data fine in the spatial resolution.

15. A nuclear medicine diagnostic apparatus according to claim 1, wherein the planar image generating circuit can generate planar image data short in data storage time and planar image data long in data storage time.

16. A nuclear medicine diagnostic apparatus according to claim 1, wherein the detector has a plurality of semiconductor cells arranged in a matrix array.

17. A nuclear medicine diagnostic apparatus according to claim 1, wherein the detector has a true coincidence counting yield of over 100 k cps.

18. A nuclear medicine diagnostic apparatus for selecting, out of events involving detection of gamma rays by detectors, an event of paired gamma rays derived from a positron RI injected into a subject and detected by the detectors and reconstructing sectional image data on the basis of count data relating to the selected event, comprising:

an incidence direction calculating circuit configured to calculate incidence directions of gamma rays on the basis of incidence positions of the gamma rays;

a storing circuit configured to store the selected event together with the incidence position and calculated incidence direction;

an input device configured to designate a desired incidence direction; and a planar image generating circuit configured to generate planar image data on the basis of count data relating to an event which is stored in the storing circuit and whose calculated incidence direction is coincident or near-coincident with the designated incidence direction.

19. A nuclear medicine diagnostic apparatus for selecting, out of events involving detection of gamma rays by detectors, an event of paired gamma rays derived from a positron RI injected into a subject and detected by the detectors and reconstructing sectional image data on the basis of count data relating to the selected event, comprising:

an incidence direction calculating circuit configured to calculate incidence directions of gamma rays on the basis of incidence positions of the gamma rays;

an input device configured to designate a desired incidence direction; and a planar image generating circuit configured to generate planar image data on the basis of calculated data relating to an event whose calculated incidence direction is coincident or near-coincident with the designated incidence direction.

20. A method for generating image data based on paired gamma rays detected by detectors provided in a nuclear medicine diagnostic apparatus, the method comprising:

storing count data with incidence positions of the paired gamma rays;

calculating incidence directions of the gamma rays based on the incidence positions; and generating planar image data based on the count data having an incidence direction coincident or near-coincident with a designated incidence direction.

* * * * *